United States Patent [19]
Shuler et al.

[11] Patent Number: 5,798,273
[45] Date of Patent: Aug. 25, 1998

[54] DIRECT READ LATERAL FLOW ASSAY FOR SMALL ANALYTES

[75] Inventors: John K. Shuler, Baltimore; Stephen J. Lovell, Towson, both of Md.; Abigail S. Fisher, Belmont; Alan J. Weiss, Acton, both of Mass.; Robert W. Rosenstein, Ellicott City, Md.

[73] Assignees: Becton Dickinson and Company, Franklin Lakes, N.J.; Millipore Corporation, Bedford, Mass.

[21] Appl. No.: 719,221

[22] Filed: Sep. 25, 1996

[51] Int. Cl.[6] .................. G01N 33/558; G01N 33/566; G01N 33/564; G01N 33/563
[52] U.S. Cl. .................. 436/514; 436/501; 436/507; 436/510; 436/512; 436/513; 435/7.5; 435/7.93
[58] Field of Search .................. 436/514, 501, 436/507, 510, 512, 513; 435/7.5, 7.93

[56] References Cited

U.S. PATENT DOCUMENTS

| | | | |
|---|---|---|---|
| 4,740,468 | 4/1988 | Weng et al. | 435/7 |
| 5,137,808 | 8/1992 | Ullman et al. | 435/7.9 |
| 5,229,073 | 7/1993 | Luo et al. | 422/56 |
| 5,591,645 | 1/1997 | Rosenstein | 436/514 |

*Primary Examiner*—Lynette F. Smith
*Assistant Examiner*—Brett Nelson
*Attorney, Agent, or Firm*—Bruce S. Weintraub

[57] ABSTRACT

The present invention relates to a method and assay device for detecting small analytes. The results of the assay can be directly read from the device, which is a lateral flow device.

32 Claims, 3 Drawing Sheets

DIRECT READ LATERAL FLOW ASSAY FOR SMALL ANALYTES

FIELD OF THE INVENTION

The present invention relates to a novel lateral flow assay and method for detecting small analytes. Results can be directly read from the assay. Small analytes for medical diagnostics can be detected by utilization of the device and method of the present invention.

BACKGROUND OF THE INVENTION

Although there are many immunoassays which exist for detection of small analytes, currently existing products which are commercially available yield "typical" competitive inhibition results, meaning, reduction of signal with increasing analyte concentration. However, the present assay, by the method and device to be described herein, yields increased signal with increasing analyte concentration.

Furthermore, presently existing products which are commercially available incorporate a read-out zone which requires the user to compare the result to a color chart. The present invention describes an assay which provides a multiple read-out: additional line(s) appear at discrete analyte concentrations.

The present invention provides an assay and method which is capable of providing a direct reading of the results of a competitive inhibition assay for small analytes.

SUMMARY OF THE INVENTION

The present invention relates to a lateral flow assay and method for detecting small analytes. In particular, this assay is typically a competitive inhibition assay. The results of this assay can be read directly from the assay device. The device is contemplated to be used to detect small analytes useful in various types of medical diagnostic tests.

BRIEF DESCRIPTION OF THE FIGURES

FIGS. 3a–3e are a schematic representation of the results of a direct read lateral flow assay for PCB with:

a) 0 ppm analyte; b) >0 and <5 ppm analyte; c) 5 ppm analyte; d) >5 and <50 ppm analyte; and e) 50 ppm analyte.

Figure 4:
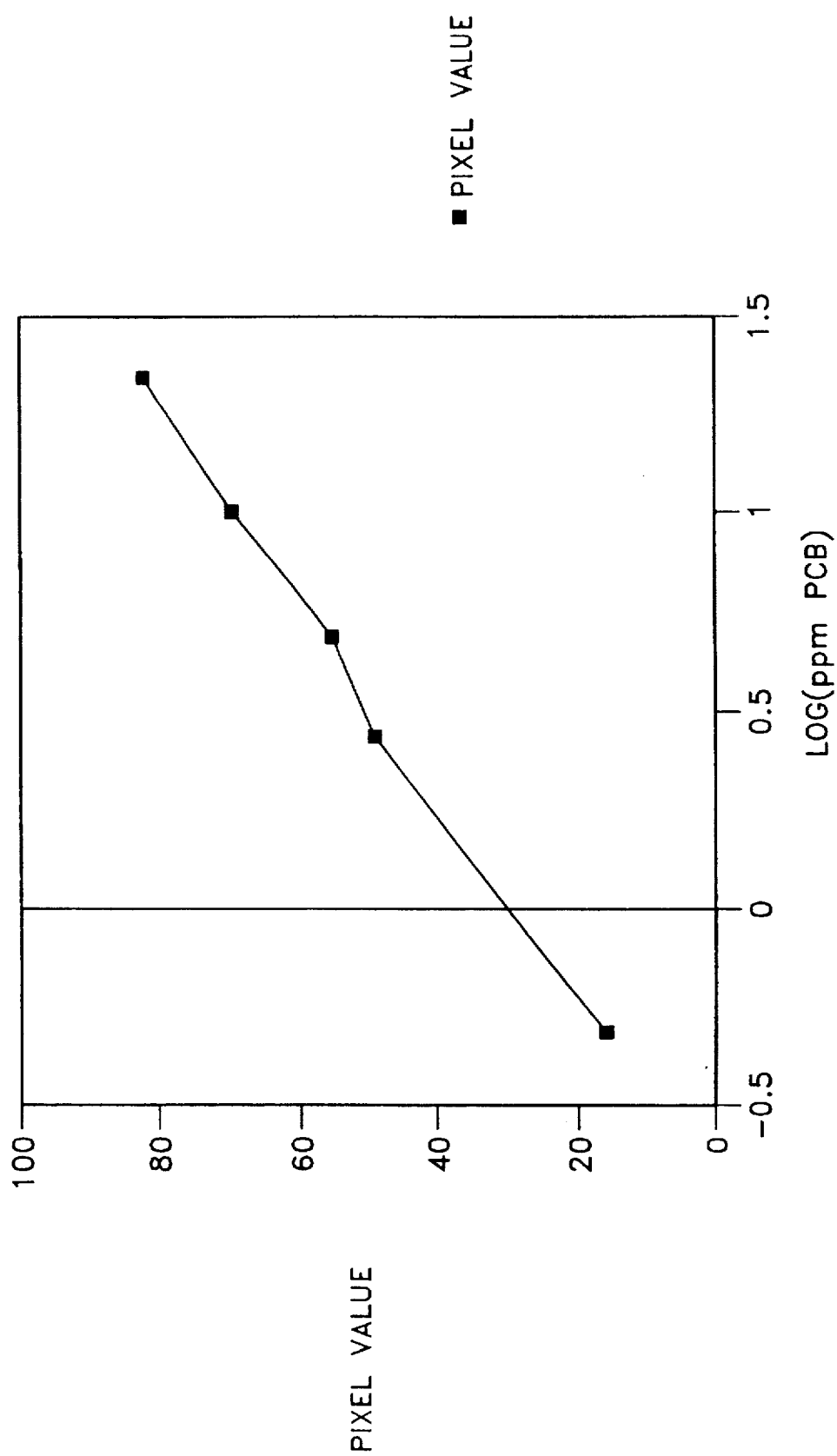

FIG. 4 is a graphic representation of the instrumented read-out line 1 in pixel intensity vs. Log [PCB].

DETAILED DESCRIPTION OF THE INVENTION

The present invention is directed to a method and device for detecting small analytes. In a preferred embodiment of the present invention, a sample (i.e., an extract or solution) suspected of containing specific analyte is added to a preparation of anti-analyte antibody which, with analyte constitutes a specific binding pair. To this mixture is added a reagent containing a tracer such as colored particles which are coated with analyte or analyte analog. Analyte or analyte analog may be attached to colored particles directly or through a carrier molecule. The colored particles will also contain an additional label which is one member of a second specific binding pair. This label may, for example, be biotin. The mixture of sample, anti-analyte antibody solution and reagent containing colored particles is applied to a lateral flow device containing a solid support (such as for example, a nitrocellulose membrane) which contains three specific areas:

1. A sample addition area;
2. A capture area containing analyte or analyte analog immobilized onto the capture area;
3. A read-out area which contains one or more zones, each zone in the read-out area containing one or more of the following: immobilized anti-analyte antibody, immobilized complementary binding partner to the label on the colored particle (e.g., antibiotin or avidin), and immobilized analyte or analyte analog.

In the case where a sample does not contain specific analyte, a fraction of the antibody binds to the tracer such as colored particles which contain analyte or analyte analog. Only a small population of particles migrate past the capture area. The minimum number of colored particles would be available for travel to and binding to materials in the zone(s) of the read-out area.

In the case where sample contains a specific analyte to be determined in the present assay, some antibody would bind to analyte and less would be available for binding to the analyte or analyte analog containing colored particles. A larger population of colored particles migrate past the capture area to bind to one or more of the zones in the read-out area. As the sample contains increasingly larger amounts of analyte, greater amounts of unbound analyte particles are free to bind to more zone(s) in the read-out area resulting in a stronger signal or the appearance of additional lines or symbols on the assay device. Results can thus be determined in both instrumented and most significantly, non-instrumented fashion.

The assay system of the present invention can detect small analytes for medical diagnostics such as nutrients (vitamins), hormones such as estrogen and progesterone, drugs of abuse, and peptides, as well as small analytes of environmental and agricultural interest such as PCB and aflatoxin. Other small analytes of interest can include, but are not limited to, trace metals and poisons such as for example, household toxins and therapeutic drugs.

Figure 1:
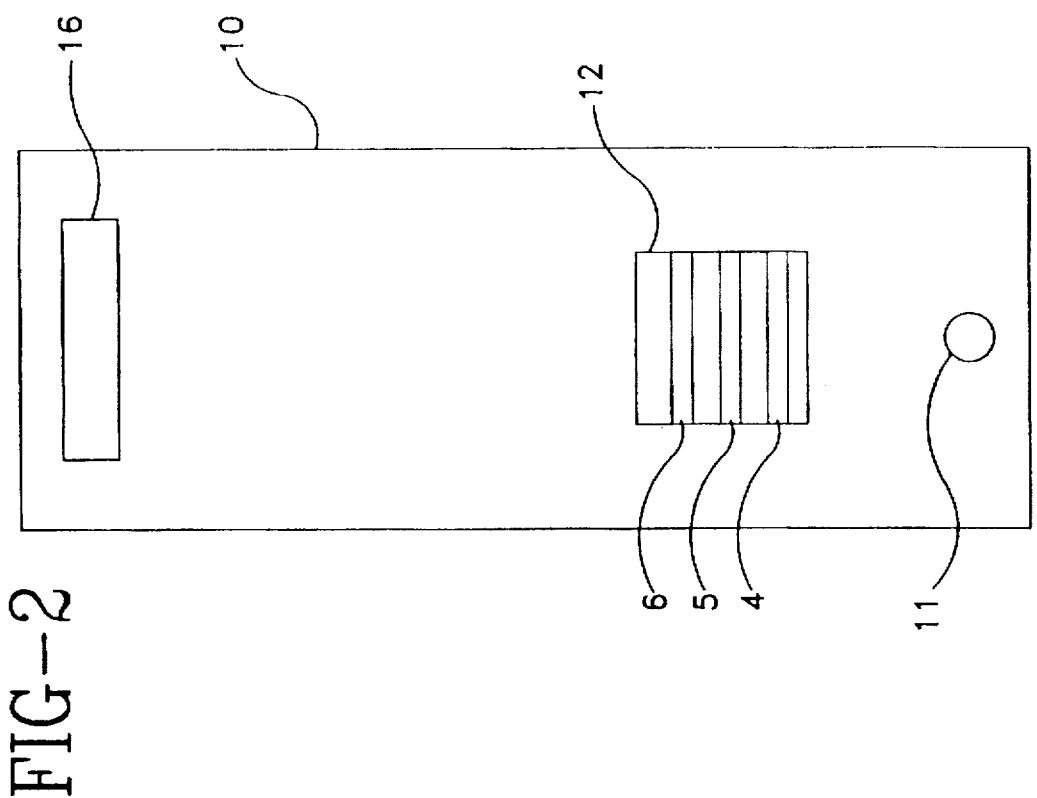
FIG. 1 is a schematic representation of a device of the present invention.

A preferred embodiment of the device of the present invention is set forth in FIG. 1. A solid support 1, which can be, for example, a nitrocellulose membrane, has a sample addition area 8; a capture area 2 having analyte or analyte analog immobilized thereon; and a read-out area 3, which contains, in this embodiment, three zones. However, it should be understood that this read-out area according to the present invention, contains at least one or more zones to provide the desired results and can contain more than three zones or less than three zones if so desired. In the embodiment set forth in FIG. 1, zone 4 is a control zone having an irrelevant anti-analyte antibody immobilized thereon wherein this is anti-analyte antibody to a second irrelevant analyte which is different than the first analyte to be determined, and wherein this irrelevant analyte is attached to a tracer which can be, for example, a colored particle. The irrelevant analyte and tracer are added to the solution/sample to be applied to the present device prior to application of that solution/sample mixture to area 8. The other zones 5 and 6 in the read-out area will have immobilized thereon complementary binding partner to the label on the colored particle. This complementary binding partner may, for example, be neutravidin. The area 7 indicates the distal end of the solid support (or strip of, for example, nitrocellulose membrane) where the assay will come to an end.

Figure 2:
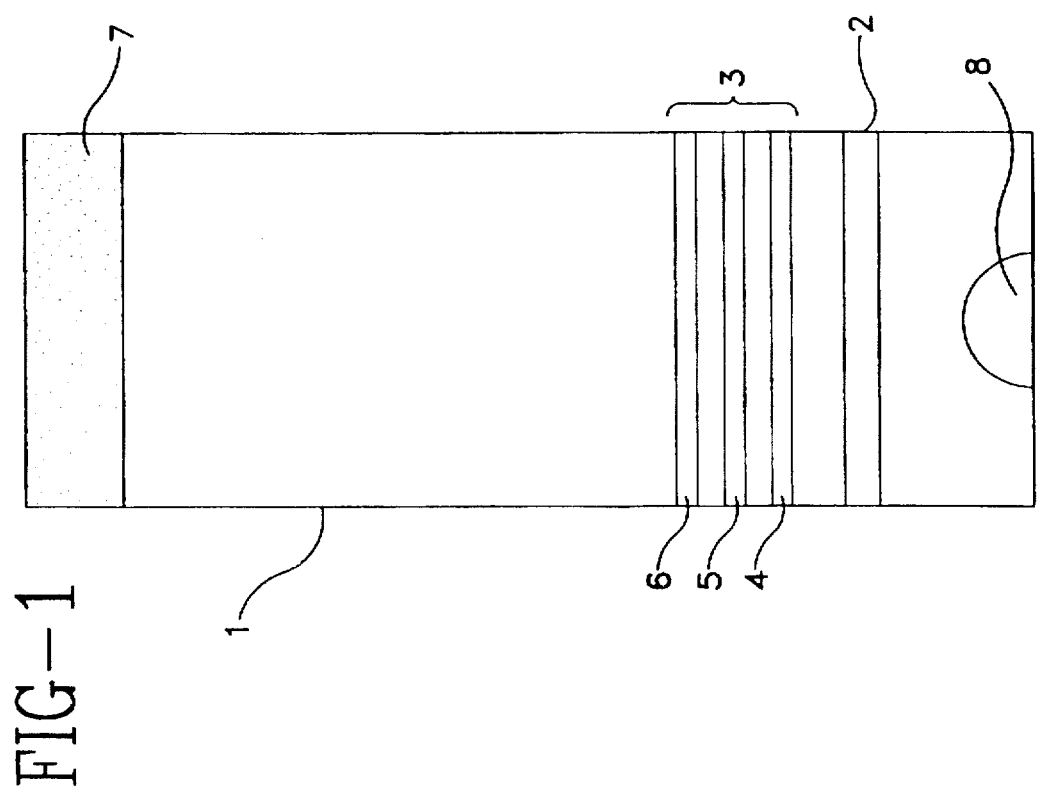
FIG. 2 is a schematic representation of another embodiment of the device of the present invention as set forth in FIG. 1.

FIG. 2 sets forth another embodiment of the device as shown in FIG. 1. In this embodiment, the solid support or strip 1 of FIG. 1 is inserted into a housing (such as, for example, a plastic housing) 10. The housing 10 has a frame having a hole 11 located at the front end of the device, and a read-out "window" 12 which encompasses a section of the read-out area 3 and zones 4, 5 and 6 shown in FIG. 1. The frame of the housing 10 also has a rectangular "window" 16 at the distal end of the plastic housing covering the solid support which will be used for viewing the end of the assay. A different tracer or marker can be added to the sample to enable the user to read the end of the assay by viewing this tracer or marker in the window 16. In the embodiment of the device set forth in FIG. 2, a section of the sample addition area can be seen through the hole 11 and a section of the read-out area can be seen through the window 12, and will show zones 4, 5 and 6. However, the capture area 2 is not visible to the naked eye. It is under the housing 10 between the hole 11 and the window 12.

The solid support which is employed in the assay is generally a cellulose ester, with nitrocellulose giving exceptionally good results. It should be understood that the term "nitrocellulose" refers to nitric acid esters of cellulose, which may be nitrocellulose alone, or a mixed ester of nitric acid and other acids, in particular, aliphatic carboxylic acids having from one to seven carbon atoms, with acetic acid being preferred. Such solid supports which are formed from cellulose esterified with nitric acid alone or a mixture of nitric acid and another acid such as acetic acid, are often referred to as nitrocellulose paper.

Although nitrocellulose is a preferred material for producing the solid support, it is to be understood that other materials, having a surface area sufficient for supporting a binder in a concentration as set forth above may also be employed for producing such solid supports including but not limited to nylon.

The solid support employed in the assay is preferably in sheet form, with the substrate in sheet form, generally being in the form of a card, a test strip or dip stick, etc. It is to be understood, however, that other forms are also within the spirit and scope of the invention.

The tracer of the present invention can be, for example, a colored particle. A preferred colored particle is a sac, which includes a dye or other colored substance as a marker, whereby the tracer, when used in the assay, is visible without destruction of the sac to release the colored substance. The sac may be any one of a wide variety of sacs, including, but not limited to intact erythrocytes, erythrocyte ghosts, liposomes (single walled, sometimes called vesicles, or multilamellar), polymer microcapsules, for example, those made by coacervation, or intrafacial polymerization, etc.

Polymer microcapsules are produced by procedures known in the art except that the solution in which the microcapsules are formed also includes a marker whereby the interior of the polymer microcapsule includes the marker. The preparation of such microcapsules is disclosed, for example, in *Microencapsulation Processes and Applications*, edited by Jan E. Vandegger (Plenum Press 1974) which is hereby incorporated by reference.

As known in the art, liposomes can be prepared from a wide variety of lipids, including phospholipids, glycolipids, steroids, relatively long chain alkyl esters, for example, alkyl phosphates, fatty acid esters, for example, lecithin, fatty amines and the like. A mixture of fatty materials may be employed, such as a combination of neutral steroid, a charged amphiphile and a phospholipid. The examples of phospholipids include lecithin, sphingomyelin, dipalmitoyl phosphatidylcholine, and the like. Steroids may include cholesterol, cholestanol, anesterol, and the like. The charged amphiphilic compounds may generally contain from twelve to thirty carbon atoms and may include mono- or dialkyl phosphate esters or an alkylamine, for example, dicetyl phosphate, stearyl amine, hexadecyl amine, dilauryl phosphate, and the like.

The liposome sacs are prepared in an aqueous solution including the marker whereby the sacs include the marker in the interior thereof. The liposome sacs are easily prepared by vigorous agitation in the solution, followed by removal of marker from the exterior of the sac. For the preparation of liposomes, see U.S. Pat. No. 4,342,826, PCT International Publication No. WO 80/01515, U.S. Pat. No. 4,539,376 and U.S. Pat. No. 4,522,803 which are hereby incorporated by reference.

The tracer including the colored particle may also be produced by using an aqueous dispersion of a hydrophobic dye or pigment, or of polymer nuclei coated with such a dye or pigment. Such tracers are described in more detail in U.S. Pat. No. 4,373,932, which is hereby incorporated by reference.

Examples of particles which may be used in the present invention include, but are not limited to, ferritin, phycoerythrins or other phycobili-proteins, precipitated or insoluble metals or alloys, fungal, algal, or bacterial pigments or derivatives such as bacterial chlorophylls, plant materials or derivatives and the like. The visible colored particles may be visible polymer particles, such as colored polystyrene particles of spherical shape (i.e., beads).

Thus the process of the present invention can be as follows, for an assay for a specific small analyte: anti-analyte antibody is mixed with tracer such as colored particles containing analyte or analyte analog on their surface, as well as a second molecule (such as biotin) also on the surface and a sample containing analyte. During the formation of a complex between anti-analyte antibody and analyte or analyte analog on the particles, the more analyte present in the sample, the more colored particles are not associated with the complex (i.e., this is the free fraction). The mixture is then applied to a lateral flow device of the present invention, consisting of a solid support such as a strip of nitrocellulose on which is deposited a line of analyte in a capture area, and one or more zones in a read-out area. As the sample enters the support, the complex is too big to flow, so it remains at the front end of the support. The particles that are "free" flow up the strip. Any particles that have anti-analyte bound to them will get trapped by the line of analyte. The remainder of the particles can be trapped by the avidin (or neutravidin or strepavidin). The more "free" particles there are, the darker the avidin line(s) become. If there are multiple avidin lines, one can also count lines as a measure of concentration of analyte in the sample. The analyte can, as stated above, be any small molecule or family of molecules, such as polychlorinated biphenyls (PCB), drugs of abuse, steroid hormones, etc. If there are analogs of analyte that bind to anti-analyte antibody at a lower affinity than the analyte does, they can be placed on the particle surface to maximize the interaction with the analyte in the sample and the anti-analyte antibody, rather than the antibody binding to the particles.

If there is no analyte in the sample, all of the particles are bound to the complex, and/or get trapped by the line of analyte in the capture area on the solid support. If this line is hidden (i.e., under the plastic housing as shown in FIG. 2), one reads no signal in the read-out area and the zone(s) therein. As the analyte in the sample increases, less complex is formed, and more particles are "free", causing a positive read. The advantage in using a binder such as biotin to effect the trapping of the "free" particles is that it binds to a molecule such as avidin with an extremely high affinity and that binding occurs very quickly. Since the analyte to be determined is, for this assay, intended to be a small molecule, it may be chemically attached to a carrier for attachment to the particle surface and/or the analyte line in the capture area on the solid support. The following Example is intended to be demonstrative and is not intended to in any way limit the present invention.

EXAMPLES

Example I

Direct Read PCB Assay

REAGENTS

1. A conjugate of PCB analog and rabbit gamma globulin (Conj1) was prepared.
2. The conjugate was coupled to carboxy blue latex particles by EDC (1-ethyl-3(3 dimethylaminopropyl) carbodiimide. The latex suspension was labeled with biotin by reaction with N-hydroxysuccinimidobiotin.
3. Anti-PBC antibody was purified from serum by protein A agarose chromatography.
4. A solution of purified anti-hCG antibody was prepared for the control system.
5. hCG was coupled to carboxy blue latex particles for the control system.
6. A 1% solution of erythosin B was prepared for an end-of-assay dye indicator.

PROCEDURE

Figure 3:
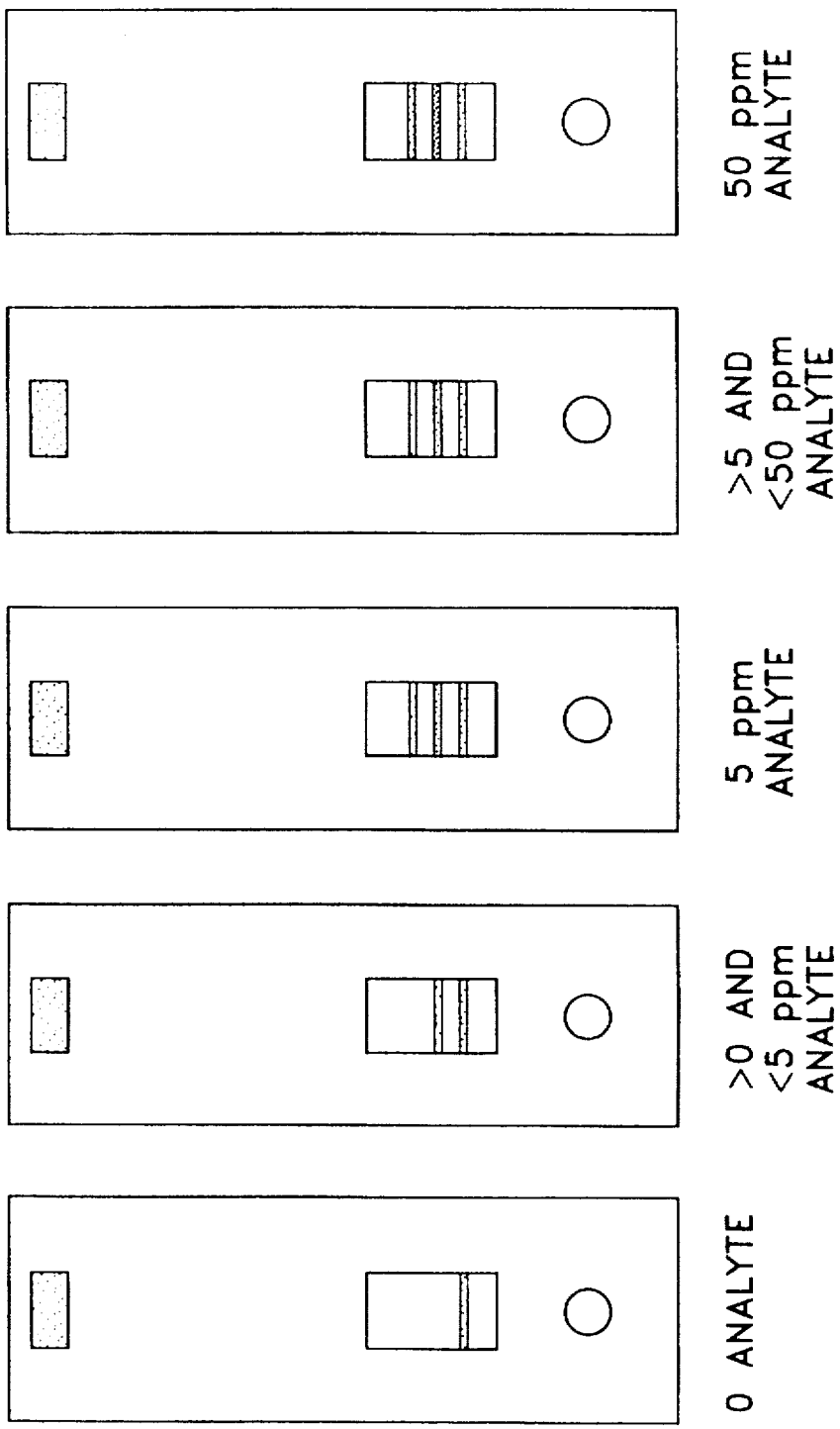

1. A strip of nitrocellulose membrane 0.7×8.2 cm was cut.
2. One line of Conj1 was applied to the nitrocellulose membrane (capture area).
3. One line of anti-hCG antibody solution was applied to the nitrocellulose membrane (control zone within the read-out area).
4. Two lines of Conj1 mixed with neutravidin were applied to the nitrocellulose membrane (two zones of read-out area).
5. One line of 1% erythosin B solution was applied close to the distal end of the strip for end-of-assay indicator.
6. The strip was dried for 60 minutes at 45° C. and a foam pad was attached at the sample end.
7. The strip was inserted into a housing with a hole located at the sample area, a window at the read-out area (including the control zone and two other zones), and a window at the distal end of the strip for reading the end-of assay marker.
8. 20 μL of ethanol extract were pipetted into a tube.
9. 50 μL of anti-PCB antibody in aqueous buffer were pipetted into the tube and mix.
10. 10 μL of a suspension of hCG latex particles and Conj1-biotin latex particles were pipetted into the tube, mixed and incubated 5 minutes at room temperature.
11. The entire suspens ion was added to the sample area of the strip (in the housing).
12. After the end-of assay window filled with red color, the results were read as follows:
    A. Multi-line visual read (shown in FIG. 3).
       i. One control line visible: 0 ppm PCB (shown in FIG. 3a).
       ii. One control line plus one read-out line (equal or greater than control line in intensity): 5 ppm PCB (shown in FIG. 3c). There is a second read-out of lesser intensity than the control line.
       iii. One control line plus two read-out lines (equal or greater than control line in intensity): 50 ppm PCB (shown in FIG. 3e). FIG. 3b shows results for between 0 and 5 ppm analyte; and FIG. 3d shows results for between 5 and 50 ppm analyte.
    B. Single line visual read (this version would have a single read-out zone (line) within the read-out area)
       i. One control line visible: 0 ppm PCB
       ii. The intensity of the read-out line was compared to an intensity chart.
    C. Single line instrumented read (this version would have a single read-out zone (line) within the read-out area with or without a control line in the read-out area)
       i. The reflectance of the read-out line was determined with a reflectance spectrophotometer.

The concentration of PCB (0, 0.5, 3, 5, 10, and 22 ppm) was read. The absorbance obtained from the Read-out line 1 from each strip was examined with Sigma Scan Image. A pixel value was determined for each strip and plotted versus the log of the PCB (ppm). The data are shown in the following Table I.

TABLE 1

| PCB ppm | Log [PCB] | Pixel Value |
|---------|-----------|-------------|
| 0.5     | −.301     | 16.3        |
| 3       | .477      | 50.4        |
| 3       | .477      | 48.7        |
| 5       | .699      | 54.3        |
| 10      | 1         | 68.8        |
| 22      | 1.342     | 81.6        |
| 22      | 1.342     | 78.7        |

These data are plotted on the graph shown in FIG. 4. A linear regression of X=log (PCB) and Y=pixel value yielded r=0.99.

What is claimed is:

1. A process for determining the presence or amount of an analyte in a sample comprising:
   a) contacting said sample with a preparation containing
      i) anti-analyte antibodies, which bind to analyte or to both analyte and an analyte analog, and
      ii) an assay tracer, wherein said assay tracer comprises a detectable particulate substance having immobilized on its surface, analyte or analyte analog and a first member of a binding pair, to provide a sample/preparation mixture containing analyte/anti-analyte antibody complexes and/or assay tracer/anti-analyte complexes;
   b) contacting said sample/preparation mixture with a sample addition area of a lateral flow device, wherein said device comprises a solid support containing, in sequence,
      i) said sample addition area,
      ii) a capture area, wherein analyte or analyte analog is immobilized, to capture said analyte/anti-analyte antibody complexes and/or assay tracer/anti-analyte complexes,
      iii) a read-out area comprising at least one zone, wherein a second member of said binding pair, which binds to said first member, is immobilized, to bind assay tracer not captured in said capture area, in proportion to the amount of analyte in said sample;
   c) allowing said sample/preparation mixture to flow through said lateral flow device; and d) detecting the presence or amount of assay tracer bound in said at least one zone of said read-out area as a measure of analyte in said sample.

2. The process of claim 1, wherein said assay tracer is a colored particle.

3. The process of claim 2, wherein said colored particle is a colored liposome or a colored polymeric bead.

4. The process of claim 3, wherein said colored polymeric bead is a colored polystyrene bead.

5. The process of claim 1, wherein said solid support comprises nitrocellulose.

6. The process of claim 1, wherein said first member of said binding pair, immobilized on said assay tracer, is biotin.

7. The process of claim 1, wherein said second member of said binding pair, immobilized in said read-out zone, is avidin, streptavidin, or neutravidin.

8. The process of claim 1, wherein:
   a) said lateral flow device further comprises a housing which covers the entire lateral flow device, wherein said housing has
      i) an opening over said sample addition area,
      ii) a first window for viewing said read-out area, and
      iii) a second window for viewing a distal end of said device; and
   b) said process further comprises contacting said sample/preparation mixture with said sample addition area by pouring said sample/preparation mixture through said opening.

9. The process of claim 8, wherein an end-of-assay tracer is added to said sample/preparation mixture for viewing through said second window.

10. The process of claim 1, wherein:
   a) said lateral flow device further comprises a second zone in said read-out area, which functions as a control, wherein an anti-control-antigen antibody is immobilized; and
   b) said process further comprises contacting a control tracer with said sample in step a), wherein said control tracer comprises a detectable particulate substance having immobilized on its surface a control antigen which binds to said anti-control-antigen antibody.

11. The process of claim 10, wherein said assay tracer and said control tracer are colored particles.

12. The process of claim 11, wherein said colored particles are colored liposomes or colored polymeric beads.

13. The process of claim 12, wherein said colored polymeric beads are colored polystyrene beads.

14. The process of claim 10, wherein said solid support comprises nitrocellulose.

15. The process of claim 10, wherein said first member of said binding pair, immobilized on said assay tracer, is biotin.

16. The process of claim 10, wherein said second member of said binding pair, immobilized in said read-out zone, is avidin, streptavidin, or neutravidin.

17. The process of claim 10, wherein:
   a) said lateral flow device further comprises a housing which covers the entire lateral flow device, wherein said housing has
      i) an opening over said sample addition area,
      ii) a first window for viewing said read-out area, and
      iii) a second window for viewing a distal end of said device; and
   b) said process further comprises contacting said sample/preparation mixture with said sample addition area by pouring said sample/preparation mixture through said opening.

18. The process of claim 17, wherein an end-of-assay tracer is added to said sample/preparation mixture for viewing through said second window.

19. A kit for determining the presence or amount of an analyte in a sample, comprising:
   a) a preparation containing
      i) anti-analyte antibodies, which bind to analyte or to both analyte and an analyte analog, and
      ii) an assay tracer, wherein said assay tracer comprises a detectable particulate substance having immobilized on its surface, analyte or analyte analog and a first member of a binding pair; and
   b) a lateral flow device, comprising a solid support containing, in sequence,
      i) said sample addition area,
      ii) a capture area, wherein analyte or an analyte analog is immobilized, and
      iii) a read-out area comprising at least one zone, wherein a second member of said binding pair, which binds to said first member, is immobilized.

20. The kit of claim 14, wherein said assay tracer is a colored particle.

21. The kit of claim 20, wherein said colored particle is a colored liposome or a colored polymeric bead.

22. The kit of claim 21, wherein said colored polymeric bead is a colored polystyrene bead.

23. The kit of claim 19, wherein said solid support comprises nitrocellulose.

24. The kit of claim 19, wherein said second member of said binding pair, immobilized in said read-out zone, is avidin, streptavidin, or neutravidin.

25. The kit of claim 19, further comprising:
   a housing which covers the entire lateral flow device, wherein said housing has
      i) an opening over said sample addition area,
      ii) a first window for viewing said read-out area, and
      iii) a second window for viewing a distal end of said device.

26. The kit of claim 19, further comprising:
   a) a second zone in said read-out area, which functions as a control, wherein an anti-control-antigen antibody is immobilized; and
   b) a control tracer comprising a detectable particulate substance having immobilized on its surface a control antigen which binds to said anti-control-antigen antibody.

27. The kit of claim 26, wherein said assay tracer and said control tracer are colored particles.

28. The kit of claim 27, wherein said colored particles are colored liposomes or colored polymeric beads.

29. The kit of claim 28, wherein said colored polymeric beads are colored polystyrene beads.

30. The kit of claim 26, wherein said solid support comprises nitrocellulose.

31. The kit of claim 26, wherein said second member of said binding pair, immobilized in said read-out zone, is avidin, streptavidin, or neutravidin.

32. The kit of claim 26, further comprising:
   a housing which covers the entire lateral flow device, wherein said housing has
      i) an opening over said sample addition area,
      ii) a first window for viewing said read-out area, and
      iii) a second window for viewing a distal end of said device.

* * * * *